US011707207B2

(12) United States Patent
Stigall et al.

(10) Patent No.: US 11,707,207 B2
(45) Date of Patent: *Jul. 25, 2023

(54) DEVICE, SYSTEM, AND METHOD FOR ASSESSING INTRAVASCULAR PRESSURE

(71) Applicant: KONINKLIJKE PHILIPS N.V., Eindhoven (NL)

(72) Inventors: Jeremy Stigall, Carlsbad, CA (US); Joseph Lauinger, San Diego, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 450 days.

This patent is subject to a terminal disclaimer.

(21) Appl. No.: 16/927,676

(22) Filed: Jul. 13, 2020

(65) Prior Publication Data

US 2020/0337595 A1    Oct. 29, 2020

Related U.S. Application Data

(63) Continuation of application No. 14/702,482, filed on May 1, 2015, now Pat. No. 10,709,357.

(Continued)

(51) Int. Cl.

| A61B 5/0215 | (2006.01) |
|---|---|
| A61B 5/107 | (2006.01) |
| A61B 8/08 | (2006.01) |
| A61B 5/00 | (2006.01) |
| A61B 8/12 | (2006.01) |

(Continued)

(52) U.S. Cl.
CPC ........ *A61B 5/1076* (2013.01); *A61B 5/02007* (2013.01); *A61B 5/0215* (2013.01); *A61B 5/6852* (2013.01); *A61B 5/7278* (2013.01); *A61B 8/0891* (2013.01); *A61B 8/12* (2013.01); *A61B 5/02158* (2013.01);

(Continued)

(58) Field of Classification Search
None
See application file for complete search history.

(56) References Cited

U.S. PATENT DOCUMENTS

| 8,012,106 B2 | 9/2011 | Mangiardi |
|---|---|---|
| 8,298,156 B2 | 10/2012 | Manstrom |

(Continued)

FOREIGN PATENT DOCUMENTS

WO    2012155040 A1    11/2012

OTHER PUBLICATIONS

Korean Intellectual Property Office, International Search report for PCT/US2015/028708 dated Aug. 13, 2015, 12 pages.

*Primary Examiner* — Luther Behringer

(57) ABSTRACT

An apparatus for assessing the severity of stenosis in a blood vessel includes an elongate body including a distal portion and a centering assembly. The centering assembly is actuatable to selectively center the elongate body in the vessel. A pressure sensor is disposed adjacent the centering assembly and is configured to detect fluid pressure in the vessel. A processing system receives the measured pressure from the pressure sensor, receives data representing the cross-sectional area of the vessel, receives data representing the size of the distal portion, calculates a offset correlation based on the size of the distal portion and based on the size of the vessel, and calculates a fractional flow reserve (FFR) for the vessel as an index of stenosis severity taking into account the offset correlation and the measured fluid pressure from the pressure sensor.

14 Claims, 3 Drawing Sheets

Related U.S. Application Data

(60) Provisional application No. 61/987,618, filed on May 2, 2014.

(51) Int. Cl.
*A61B 5/02* (2006.01)
*A61B 8/00* (2006.01)
*A61B 8/06* (2006.01)

(52) U.S. Cl.
CPC .......... *A61B 5/6886* (2013.01); *A61B 5/7435* (2013.01); *A61B 8/06* (2013.01); *A61B 8/445* (2013.01)

(56) References Cited

U.S. PATENT DOCUMENTS

| | | |
|---|---|---|
| 8,485,985 B2 | 7/2013 | Manstrom |
| 2005/0010138 A1 | 1/2005 | Mangiardi |
| 2006/0064039 A1 | 3/2006 | Griego et al. |
| 2010/0241069 A1 | 9/2010 | Hatten |
| 2011/0092955 A1 | 4/2011 | Purdy |
| 2013/0131523 A1 | 5/2013 | Suchecki |
| 2013/0303914 A1 | 11/2013 | Hiltner |
| 2014/0005521 A1 | 1/2014 | Koehler |

…

DEVICE, SYSTEM, AND METHOD FOR ASSESSING INTRAVASCULAR PRESSURE

CROSS REFERENCE TO RELATED APPLICATIONS

The present application is a continuation of U.S. application Ser. No. 14/702,482, filed May 1, 2015, now U.S. Pat. No. 10,709,357, which claims priority to and the benefit of the U.S. Provisional Patent Application No. 61/987,618, filed May 2, 2014, each of which are hereby incorporated by reference in their entireties.

TECHNICAL FIELD

Embodiments of the present disclosure relate generally to the field of medical devices and, more particularly, to a device, system, and method for assessing pressure within vessels. In particular, the present disclosure relates to the assessment of the severity of a blockage or other restriction to the flow of fluid through a vessel. Aspects of the present disclosure are particularly suited for evaluation of biological vessels in some instances. For example, some particular embodiments of the present disclosure are specifically configured for the evaluation of a stenosis of a human blood vessel.

BACKGROUND

Heart disease is a serious health condition affecting millions of people worldwide. One major cause of heart disease is the presence of blockages or lesions within the blood vessels that reduce blood flow through the vessels. Traditionally, surgeons have relied on X-ray fluoroscopic (planar) images to show the external shape or silhouette of the blood vessels to guide treatment. Unfortunately, using only X-ray fluoroscopic images lends a great deal of uncertainty about the exact extent and orientation of the lesion responsible for the occlusion, making it difficult to find the exact location of the stenosis for treatment. In addition, X-ray fluoroscopy is an inadequate reassessment tool to evaluate the vessel after surgical treatment.

A currently accepted technique for assessing the severity of a stenosis in a blood vessel, including ischemia-causing lesions, is fractional flow reserve (FFR). FFR is defined as the ratio of the maximal blood flow in a stenotic artery, taken distal to the lesion, to normal maximal flow. Accordingly, to calculate the FFR for a given stenosis, two blood pressure measurements are taken: one measurement distal or downstream to the stenosis and one measurement proximal or upstream to the stenosis. FFR is a calculation of the ratio of the distal pressure measurement relative to the proximal pressure measurement. FFR provides an index of stenosis severity that allows determination as to whether the blockage limits blood flow within the vessel to an extent that treatment is required. The more restrictive the stenosis, the greater the pressure drop across the stenosis, and the lower the resulting FFR. FFR measurements can be used as a decision point for guiding treatment decisions. The normal value of FFR in a healthy vessel is 1.00, while values less than about 0.80 are generally deemed significant and require treatment. Common treatment options include angioplasty, atherectomy, and stenting.

One method of measuring the pressure gradient across a lesion is to use a pressure-sensing guidewire that has a pressure sensor embedded within the guidewire itself. A user may initially position the pressure sensor of the guidewire distal to the lesion and measure the distal pressure before drawing the guidewire backwards to reposition the sensor proximal to the lesion to measure the proximal pressure. This method has the disadvantages of inaccurate pressure readings due to drift and increased susceptibility to thermal variations, high manufacturing costs, and time-consuming repositioning steps (especially in situations involving multiple lesions). Further, pressure-sensing guidewires often suffer from reduced precision and accuracy in making intravascular pressure measurements when compared to larger pressure-sensing devices, such as aortic pressure-sensing catheters.

Another method of measuring the pressure gradient across a lesion is to use a small catheter connected to a blood pressure sensor, which is often contained in a sensor housing associated with the catheter. However, this method can introduce error into the FFR measurement because as the catheter crosses the lesion, the catheter and the sensor housing themselves create additional blockage to blood flow across the lesion and contributes to a lower distal blood pressure than what would be caused by the lesion alone, which may exaggerate the measured pressure gradient across the lesion.

While the existing treatments have been generally adequate for their intended purposes, they have not been entirely satisfactory in all respects. The devices, systems, and associated methods of the present disclosure overcome one or more of the shortcomings of the prior art.

SUMMARY

The present disclosure relates generally to a device, systems, and methods of using a pressure-sensing catheter for the assessment of intravascular pressure, including, by way of non-limiting example, the calculation of an FFR value. In some instances, embodiments of the present disclosure are configured to measure the pressure proximal to and distal to a stenotic lesion within a blood vessel. Embodiments of the present disclosure include a pressure sensor embedded in the wall of the catheter, which may include a movable sleeve capable of smoothing the outer diameter of the sensing catheter. In some embodiments, the pressure-sensing catheter disclosed herein is configured as a monorail or rapid exchange catheter where the guidewire exits the catheter body adjacent the distal end. In other embodiments, the pressure-sensing catheter disclosed herein is configured as a conventional over-the-wire catheter. The pressure-sensing catheters disclosed herein enable the user to obtain pressure measurements using an existing guidewire (e.g., a conventional 0.014 inch guidewire) that can remain fairly stationary through the pressure measurement procedure. Thus, the pressure-sensing catheters disclosed herein enable the user to obtain physiologic information about an intravascular lesion upon pullback of the catheter without losing the original position of the guidewire.

According to an exemplary aspect, the present disclosure is directed to an apparatus for assessing the severity of stenosis in a blood vessel. The apparatus includes an elongate body including a proximal portion and a distal portion, the body defining a lumen extending through at least the distal portion, the lumen sized and shaped to allow the passage of a guidewire therethrough. The apparatus also includes a centering assembly disposed at the distal portion of the elongate body, the centering assembly being actuatable to selectively center the elongate body in the vessel. A pressure sensor is disposed adjacent the centering assembly and is configured to detect fluid pressure in the vessel.

A processing system receives the measured pressure from the pressure sensor, receives data representing the cross-sectional area of the vessel, receives data representing the size of the distal portion, calculates an offset correlation based on the size of the distal portion and based on the size of the vessel, and calculates a fractional flow reserve (FFR) for the vessel as an index of stenosis severity taking into account the offset correlation and the measured fluid pressure from the pressure sensor.

In an aspect, the apparatus includes a user interface, the FFR being displayed to a clinician on the user interface. In an aspect, the processing system is configured to receive data representing the size of the vessel based on measurements taken by the centering assembly. In an aspect, the processing system is configured to cooperate with the centering assembly to determine the size of the vessel. In an aspect, the offset correlation is based on a ratio of the distal portion size to the vessel size. In an aspect, the size of the distal portion and vessel size are diametrical measurements.

According to an exemplary aspect, the present disclosure is directed to a method of assessing the severity of a stenosis in a blood vessel. The method includes actuating a centering assembly on a catheter to position the catheter centrally within a blood vessel; measuring a fluid pressure within the blood vessel using a pressure sensor on the catheter; receiving the measured fluid pressure at a processing system; receiving data indicative of the vessel cross-sectional area at the processing system; receiving data indicative of the catheter size at the processing system; calculating an offset correlation based on the diameter of the catheter and the diameter of the vessel; and determining a fractional flow reserve (FFR) for the vessel as an index of stenosis severity taking into account the offset correlation and the measured fluid pressure.

In an aspect, the method includes measuring the vessel using the centering assembly, and wherein receiving data indicative of the vessel size comprises receiving data obtained when measuring the vessel using the centering assembly. In an aspect, the centering assembly comprises an expandable portion configured to contact the inner walls of the blood vessel, the method comprising: determining the size of the centering assembly when the centering assembly is in contact with the inner walls, and wherein receiving data indicative of the vessel size comprises receiving data representing the determined size of the centering assembly. In an aspect, the expandable portion comprises a proximal expandable portion fixed in place relative to the catheter and a distal expandable portion moveable on the catheter. In an aspect, the expandable portion comprises legs extending between the proximal expandable portion and the distal expandable portion, the legs being flexible to expand radially outwardly when the distal expandable portion is moved relative to the proximal expandable portion. In an aspect, the method includes determining the size of the vessel with an IVUS imaging array disposed on the catheter. In an aspect, receiving data indicative of the catheter size comprises receiving an input from a user interface indicating the catheter size. In an aspect, receiving data indicative of the catheter size comprises accessing the catheter size previously stored in memory. In an aspect, receiving data indicative of the catheter size comprises automatically receiving the catheter size when the catheter is connected to the processing system.

According to an exemplary aspect, the present disclosure is directed to a method that includes actuating a centering assembly on a catheter to position the catheter centrally within a blood vessel; measuring a fluid pressure within the blood vessel using a pressure sensor on the catheter; receiving the measured fluid pressure at a processing system; detecting the vessel size and communicating data indicative of the vessel size at the processing system; receiving data indicative of the catheter size at the processing system; calculating an offset correlation based on the diameter of the catheter and the diameter of the vessel; and determining a fractional flow reserve (FFR) for the vessel as an index of stenosis severity taking into account the offset correlation and the measured fluid pressure.

In an aspect, the method includes measuring the vessel using the centering assembly, and wherein receiving data indicative of the vessel size comprises receiving data obtained when measuring the vessel using the centering assembly. In an aspect, the centering assembly comprises an expandable portion configured to contact the inner walls of the blood vessel, the method comprising: determining the size of the centering assembly when the centering assembly is in contact with the inner walls, and wherein receiving data indicative of the vessel size comprises receiving data representing the determined size of the centering assembly. In an aspect, the expandable portion comprises a proximal expandable portion fixed in place relative to the catheter and a distal expandable portion moveable on the catheter. In an aspect, the expandable portion comprises legs extending between the proximal expandable portion and the distal expandable portion, the legs being flexible to expand radially outwardly when the distal expandable portion is moved relative to the proximal expandable portion.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
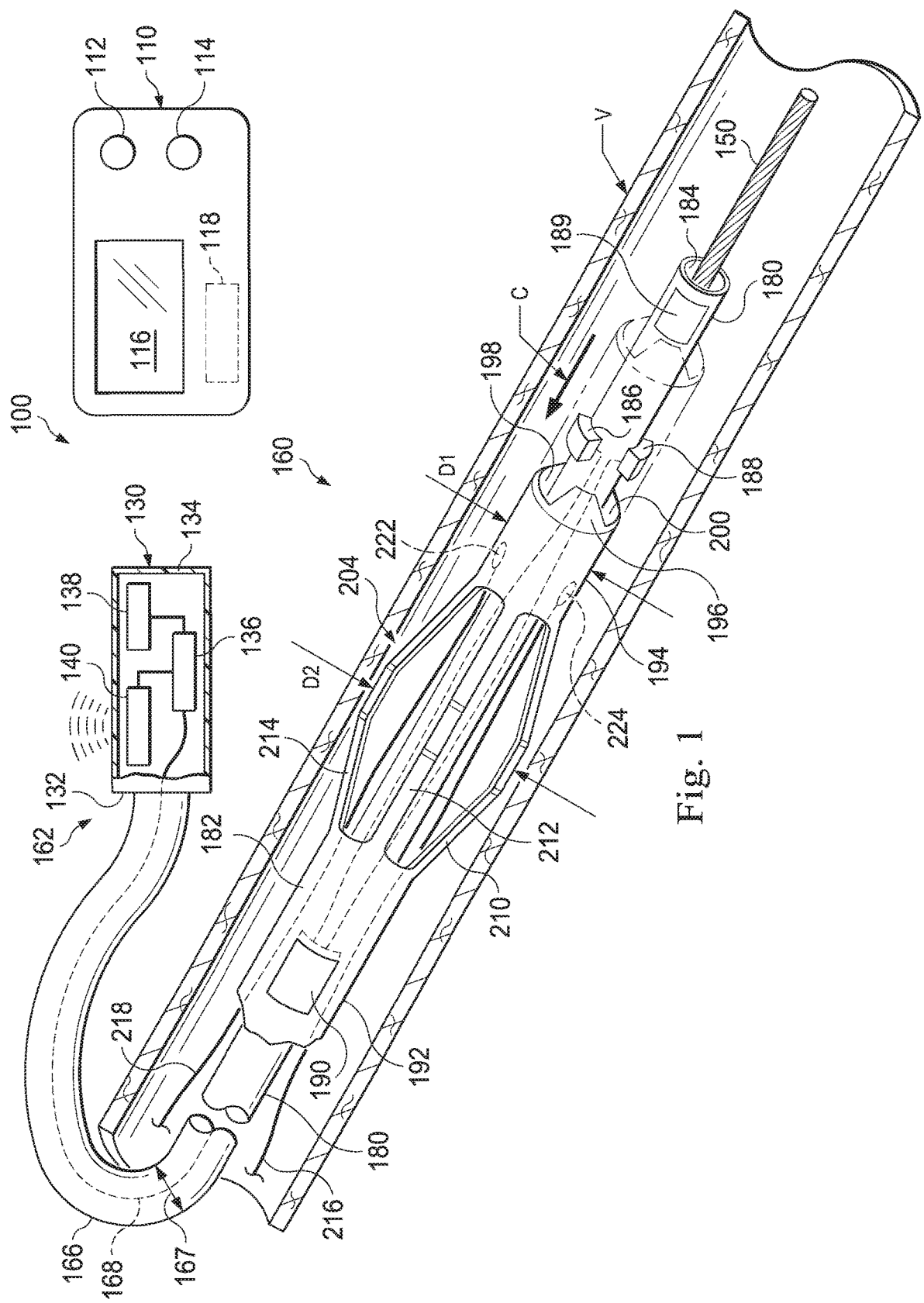
FIG. 1 is a diagrammatic partial perspective view of a sensing system according to one embodiment of the invention.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. For the sake of brevity, however, the numerous iterations of these combinations will not be described separately. For simplicity, in some instances the same reference numbers are used throughout the drawings to refer to the same or like parts.

The present disclosure relates generally to devices, systems, and methods of using a pressure-sensing catheter for the assessment of intravascular pressure, including, by way of non-limiting example, the calculation of an FFR value. Accordingly, the devices, systems, and methods may make measurements of pressure, flow, or other factors, and calculate the FFR value. In some instances, the devices, systems, and methods include determining an offset correlation based on the size (e.g., diameter) of the pressure-sensing catheter and the size (e.g., diameter) of the blood vessel. The offset correlation is then used as an input to calculate the FFR, making the FFR a more accurate prediction of stenosis severity than is accomplished when FFR is calculated only based on the size of the pressure-sensing catheter. In some instances, the pressure-sensing catheter itself is configured to measure or detect information for calculating the size of the vessel. In some instances, embodiments of the present disclosure are configured to measure the pressure proximal to and distal to a stenotic lesion within a blood vessel.

Embodiments of the present disclosure include a pressure-sensing catheter having one or more pressure sensors disposed under a movable sleeve capable of smoothing the outer diameter of the sensing catheter. In some embodiments, the pressure-sensing catheter disclosed herein is configured as a monorail or rapid exchange catheter with a guidewire lumen extending along a distal portion such that the guidewire exits the catheter body adjacent the distal end. In other embodiments, the pressure-sensing catheter disclosed herein is configured as a conventional over-the-wire catheter with the guidewire lumen extending the length of the catheter. The pressure-sensing catheters disclosed herein enable the user to obtain pressure measurements using an existing guidewire (e.g., a conventional 0.014 inch guidewire) that can remain fairly stationary through the pressure measurement procedure. Thus, the pressure-sensing catheters disclosed herein enable the user to obtain physiologic information about an intravascular lesion upon pullback of the catheter without losing the original position of the guidewire.

FIG. 1 illustrates a medical system 100 that is configured to measure pressure within a tubular structure V (e.g., a blood vessel) according to one embodiment of the present disclosure. In some embodiments, the medical system 100 is configured to calculate FFR based on the obtained pressure measurements. The system 100 includes a pressure-sensing catheter 160 interconnected with a processing and communication system 130 that is communicatively coupled to a user interface 110.

Figure 2:
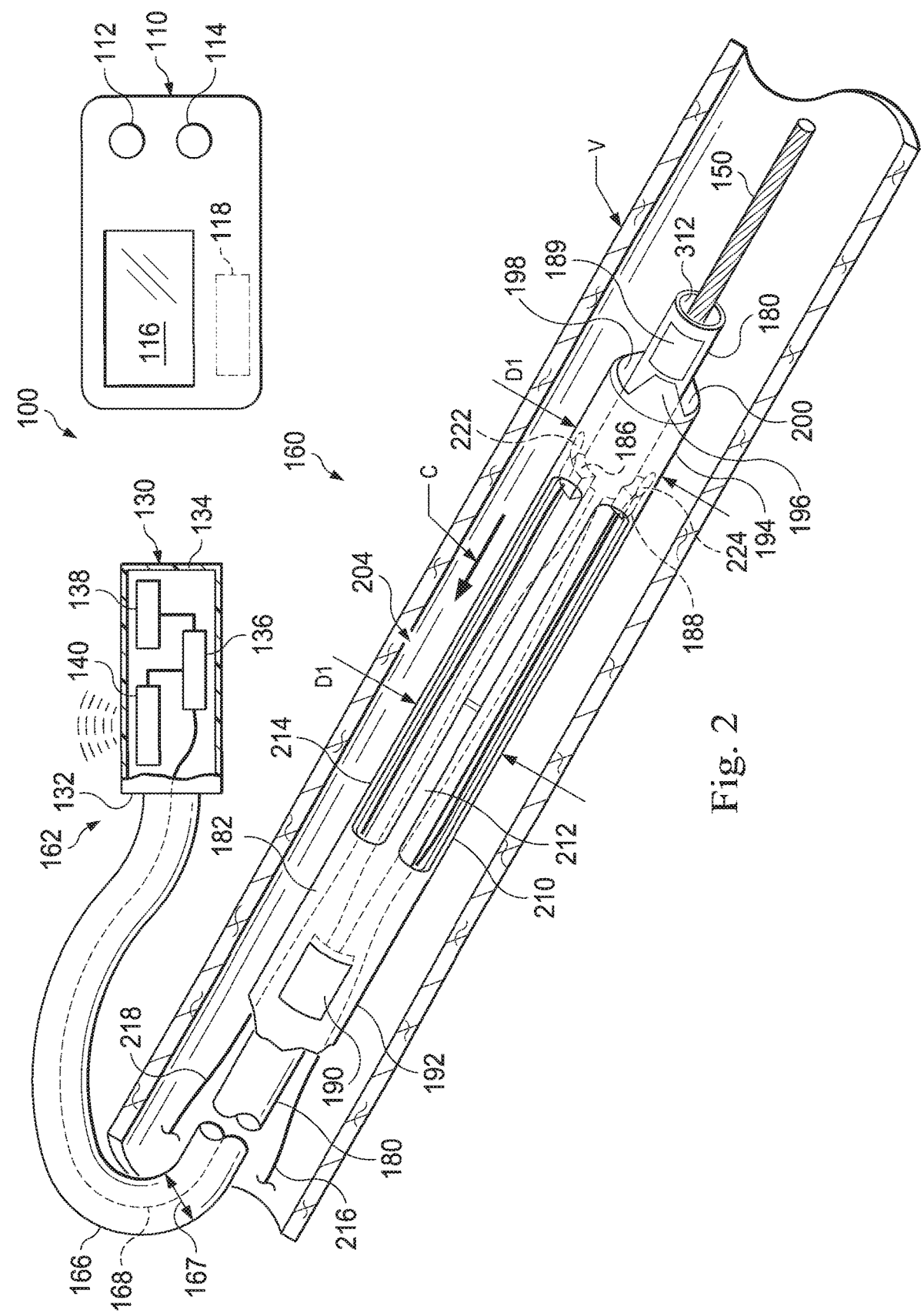
FIG. 2 is a partial perspective view of a sensing catheter of FIG. 1 in a non-deployed condition according to another aspect of the present invention.

FIG. 1 illustrates the pressure-sensing catheter 160 in a centering configuration, while FIG. 2 illustrates the pressure sending catheter 160 in a standard, non-deployed condition. With reference to both FIGS. 1 and 2, the pressure-sensing catheter 160 includes an inner catheter 180 and an outer catheter 182. The inner catheter has an inner lumen 184 configured to receive a guidewire 150. Sensors 186 and 188 are mounted on the outside of catheter 180 and extend outwardly therefrom. At least one of the sensors 186 and 188 is a pressure sensor configured to sense pressure within the vasculature of a patient undergoing treatment. The sensors 186 and 188 are electrically connected to an application specific integrated circuit (ASIC) 190 which can process analog signals from the sensor and transmit corresponding data signals to the proximal end of the catheter.

For this embodiment and other embodiments disclosed herein, the sensors 186 and 188 comprise any type of pressure sensor that is sufficiently stress resistant to maintain functionality while embedded within or on a wall of the inner catheter 180. For example, the pressure sensors 186 and 188 may each comprise a capacitive sensor, a piezoresistive pressure transducer, a fiber optic pressure sensor such as disclosed in U.S. Pat. Nos. 8,298,156 and 8,485,985 and U.S. Patent Application Publication Nos. 2013/0303914 published Nov. 14, 2013 and 2013/0131523 published on May 23, 2013 (each incorporated by reference herein in their entirety), a sensor with a silicon backbone, or any other type of pressure sensor having the requisite durability and stress resistance. In some instances, the pressure sensors 186 and 188 include an array or plurality of sensor elements (e.g., a capacitive pressure sensor array). In some embodiments, the pressure sensors 186 and 188 include a sensor diaphragm assembly. In some embodiments, the sensor diaphragm assembly includes a body having a recess covered by a flexible diaphragm configured to measure fluid pressure. The diaphragm may flex in response to variations in pressure around the diaphragm, thereby reflecting variations in blood pressure, for example. The pressure sensors 186 and 188 can then measure and transmit the variations in pressure imparted on the diaphragm assembly. Still further, although the illustrated catheter is described in terms of a pressure sensor, it is contemplated that the type of sensing element disposed on the catheter is not a limitation with respect to all of the teachings of the present disclosure. More specifically, it is contemplated that while one sensor on the catheter may be a pressure sensor, an additional one or more imaging or flow sensors can be incorporated as the sensors of the present disclosure. For example, one of the pressure sensors 186 and 188 could be an ultrasonic transducer that can image the surrounding vessel such as by intravascular ultrasound (IVUS) and/or detect fluid flow in the vessel.

In the embodiment shown, the pressure-sensing catheter includes a separate IVUS array 189 for imaging the surrounding vessel. In this embodiment, the IVUS array 189 is disposed on the inner catheter 180 at a location distal of the pressure sensors 186 and 188. In some embodiments, imaging captured by the IVUS array may be used to determine the size, cross-sectional area, and shape, such as an internal lumen perimeter or vessel diameter, which may then be used to calculate the FFR for the vessel. The IVUS array 189 may be a solid-state IVUS array such as an ultrasound scanner assembly that includes an array of ultrasound transducers distributed around the circumference of the inner catheter 180 and connected to a set of transducer control circuits such as ASIC 190. The transducer control circuits select individual transducers for transmitting an ultrasound pulse and for receiving an echo signal. By stepping through a sequence of transmitter-receiver pairs, the solid-state IVUS system can synthesize the effect of a mechanically scanned transducer element but without moving parts. The solid-state IVUS array 189 can be in electrical communication with the processing and communication system 130. Additional information about the catheter and the system associated therewith may be found in U.S. Patent Application No. 61/913,065, filed Dec. 6, 2013, incorporated herein by reference.

In the pictured embodiment, the pressure sensors 186 and 188 are mounted on and extend from the outer surface of the inner catheter 180. However, other embodiments have sensor recesses defined within a wall of the inner catheter 180, and the sensors are positioned within the recesses. The pressure sensors 186 and 188 may be coupled to the surface of the catheter 180 using any of a variety of known connection methods, including by way of non-limiting example, welding, biologically-compatible adhesive, and/or mechanical fasteners. For example, in one embodiment, the pressure sensors 186 and 188 are adhesively bonded to the inner catheter 180 using Loctite® 3311 or any other biologically compatible adhesive. In some embodiments, the sensors may be integrally formed with the catheter wall.

The outer catheter 182 is mounted about inner catheter 180. It includes a proximal portion 192 fixed in relation to the inner catheter 180 and includes a distal portion 194 moveably disposed relative to the inner catheter 180. The proximal portion 192 may be fixed in relation to the inner catheter 180 in any number of ways including, for example, being connected directly to the inner catheter 180 and being connected to other structures fixed in place relative to the inner catheter 180. In some embodiments, the proximal portion 192 of the outer catheter 182 is rigidly coupled to the inner catheter 180, such as by a weld, an adhesive or other method. The distal portion 194 of the outer catheter 182 extends about the inner catheter 180 in a sliding manner, and is configured to displace axially relative to the inner catheter 180. It includes a leading tapered end 196 that may help the catheter 160 smoothly advance through a patient's vasculature. A pair of grooves 198 and 200 in the distal portion 194 is sized to slidably receive the sensors 186 and 188, respectively, protruding from the inner catheter 180. Here, the entrance to each groove 198 and 200 begins in the tapered end 196.

A centering assembly 204 is disposed between the proximal portion 192 and the distal portion 194 of the outer catheter 182. The centering assembly 204 may be an integral portion of the outer catheter 182 or may be a separate assembly cooperatively disposed to slide the distal portion 194 relative to the inner catheter 180. In the illustrated embodiment, the centering assembly 204 includes a plurality of elongated deformable legs 210, 212, and 214 defined by cutting elongated apertures in the outer catheter 182. Pull wires 216 and 218 extend through one or more lumens within the outer catheter 182, past the deformable legs 210, 212, and 214 and are anchored in the distal portion 194 at anchor points 222 and 224, respectively. In some embodiments, the centering assembly 204 includes sensors associated therewith that detect the actual displacement of the legs 210, 212, and 214. The sensor information may then be used to calculate the actual diameter of the centering assembly 204. As described below, this may be used to estimate or measure the diameter of the target vessel, which may be used to calculate the FFR. In some embodiments, markings on the proximal catheter body 166 may indicate amount of pullwire 216 and 218 movement. The amount of movement may be correlated to the degree or level of expansion of the centering assembly 204 and may provide a value representing the size or cross-sectional area of the vessel.

The catheter 160 may also include an inner catheter body 166 that may be disposed within or may extend from the inner catheter toward the processing and communication system 130. Conductors 168 extend from the processing and communication system 130, and may be disposed adjacent to or within the catheter body 166. The conductors 168 may be coupled to the ASIC 190, the sensors 186 and 188, and/or the IVUS array 189. In some embodiments, the body 166 comprises a catheter wall that defines an internal lumen configured to receive the conductors 168.

The processing and communication system 130 includes a processor 136 structurally configured to calculate FFR based on information and data received or otherwise programmed into the processing and communication system 130. The processing and communication system 130 also performs signal processing and provides power to the ASIC 190 and the sensors 186 and 188 and the IVUS array 189. Battery 138 powers ASIC 190 and transmitter 140 communicates wirelessly with user interface 110 in a standard format such as WiFi or Bluetooth®. The ASIC 190 can provide energizing signals to the sensors 186 and 188 along conductors 168. In one aspect, sensors 186 and 188 are resistive pressure sensors that send analog signals to the ASIC 190, which then processes the signals and provides digital signals to the transmitter 140. In one aspect, the proximal portion 192 of the catheter 160 is integrally formed with the processing and communication system 130 such that an end wall 132 extends directly from catheter body 166 into an enlarged housing area 134 containing the power, processing and communication features of the system. It will be appreciated that the catheter, including the communication and processing system 130, can be a unitary, water tight outer surface surrounding the components and that the entire system can be made as a single use disposable item. In some embodiments, the processing and communication system 130 is in communication with the sensors disposed about the catheter 160, including those that may detect the position of the centering assembly 204.

The user interface 110 includes a wireless communication receiver 118 configured to receive signals from the transmitter 140. The user interface 110 includes processing components (not shown) that can control the display 116 and receive user inputs from buttons 112 and 114. In one form, the raw data provided by the catheter 160 and the processing and communication system 130 is displayed directly on display 116. In another form, the user interface 110 is controlled by a user through inputs 112 and 114 to collect sufficient data to calculate a fractional flow reserve (FFR) for a vessel and display that information to the user.

In general, the catheter 160 is sized and shaped for use within an internal structure of a patient, including but not limited to a patient's arteries, veins, heart chambers, neurovascular structures, gastrointestinal system, pulmonary system, and/or other areas where internal access of patient anatomy is desirable. In the pictured embodiment, the catheter 160 is shaped and sized for intravascular placement.

In particular, the catheter 160 is shaped and configured for insertion into a lumen of a blood vessel V such that a longitudinal axis of the catheter aligns with a longitudinal axis of the vessel at any given position within the vessel lumen. In that regard, the configuration illustrated in FIG. 1 is for exemplary purposes only and in no way limits the manner in which the catheter may curve in other instances. Generally, the elongate body may be configured to take on any desired arcuate profile when in the curved configuration. The catheter is formed of a flexible material such as, by way of non-limiting example, plastics, high density polyethylene, polytetrafluoroethylene (PTFE), Nylon, block copolymers of polyamide and polyether (e.g., PEBAX), thermoplastic, polyimide, silicone, elastomers, metals, shape memory alloys, polyolefin, polyether-ester copolymer, polyurethane, polyvinyl chloride, combinations thereof, or any other suitable material for the manufacture of flexible, elongate catheters.

The medical system 100 is configured to determine the FFR using data detected by the sensing catheter 160, and the processing that occurs at the processing and communication system 130. Still with reference to FIGS. 1 and 2, the processor 136 is configured to calculate the FFR for the particular blood vessel to provide a value that may be used to determine whether any blockage in the blood vessel restricts flow to an extent that treatment is desired. In this embodiment however, the processor 136 is configured to receive signals indicative of pressure in the blood vessel, to receive signals indicative of the size of the blood vessel, and to determine the FFR taking into account the blockage or restriction induced by use of the catheter itself. In taking the impact of the catheter into account, the processor 136 relies upon calculations that take into account the size of the catheter itself, but also takes into account the size of the vessel. For example, the system of the present disclosure corrects FFR determinations by using an offset correlation based on the diameter of the catheter 160 relative to the diameter of the target blood vessel, and automatically applies that correlation factor to any determined FFR measurement. In some embodiments, while the size of the catheter 160 may be a known value that may be entered by the surgeon, may be recognized by the system, or may be hard-coded into the system, the size of the vessel must be determined.

In some embodiments, this is done using the expandable centering assembly 204 disclosed in FIGS. 1 and 2. In some embodiments, the centering assembly 204 is configured to measure the blood vessel. For example, the processing and communication system 130 may monitor the expansion of the legs 210, 212, 214 and based on feedback, determine the diameter of the vessel. With the vessel size known, the system may be configured to calculate the FFR taking into account both the size of the catheter and the size of the vessel, thereby providing a more accurate FFR than was previously obtained. This increased accuracy in the FFR may improve accuracy of diagnoses.

Figure 3:
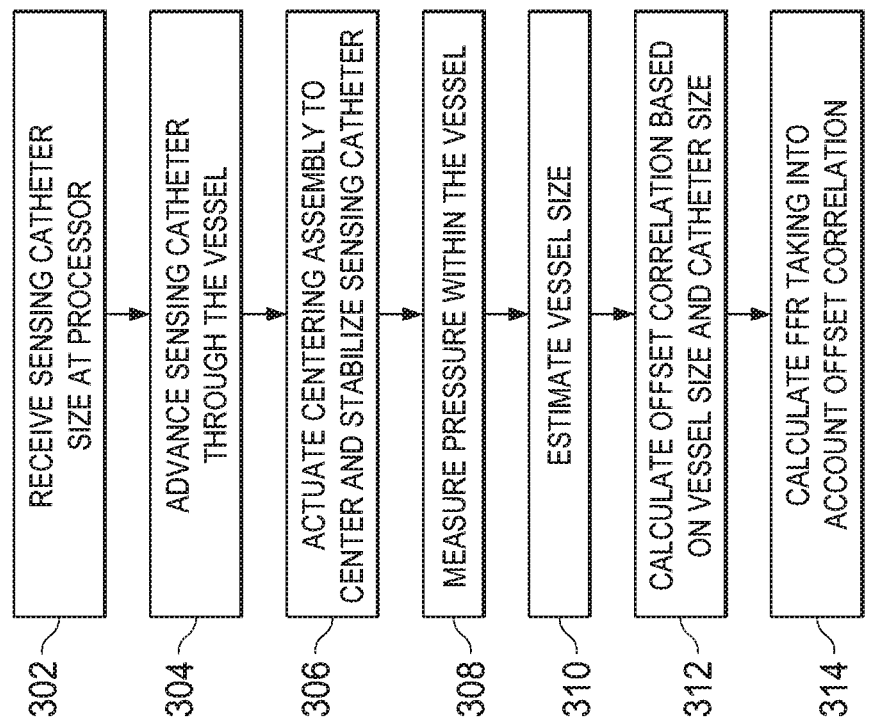
FIG. 3 is flow chart illustrating an exemplary method for determining a flow rate according to an aspect of the present invention.

FIG. 3 describes an exemplary method 300 of determining FFR. The method starts at 302 with the processor 136 receiving the catheter size. In some embodiments, the catheter size is the diameter of the distal portion of the catheter but may by any dimension or value representing the size, area, volume or structure of the catheter that may impact flow through the vessel. In some embodiments, the processor 136 receives the catheter size when it is manually input by the surgeon at the user interface 110. In some embodiments, the processor 136 receives the catheter size when it is input or stored in the processor during manufacturing or setup of the medical device system 100. In some embodiments, the processor 136 receives the catheter size when it is automatically identified when a self-identifying catheter is associated with the processing and communication system 130. Other methods for identifying the catheter size are also contemplated.

At 304, the sensing catheter 160 is advanced through the vessel toward a target region or area of interest in the patient. This may be a target area forming a part of the patient's vasculature, but may also be other parts of the patient's body. In some embodiments, the sensing catheter is advanced over a guidewire, such as the guidewire 150 in FIG. 1.

After the catheter is located at the target area, at 306, the centering assembly 204 is activated. This step will be described relative to the embodiment shown in FIG. 1, recognizing that it may be performed using any centering assembly.

The centering assembly 204 in FIG. 1 is initially in a collapsed condition having an outer diameter substantially matching diameter D1, as is shown in FIG. 2. In one aspect, the material of outer catheter 182 has sufficient resiliency such that when no force is applied to the pull wires 216 and 218, the centering assembly is biased to return to the collapsed configuration. When force is applied to the pull wires 216 and 218 in the direction of arrow C, the distal portion 194 slides longitudinally along the inner catheter 180 to the position in FIG. 1 to expose the sensors 186 and 188. Since the distal portion 194 of the outer catheter 182 is fixed in relation to the inner catheter 180, the elongated legs 210, 212, and 214 (along with one or more additional legs not shown), deform outwardly to the centering configuration illustrated in FIG. 1. In the centering configuration the legs have an outer diameter of D2 that is substantially larger than diameter D1. Thus, as shown, the centering assembly 204 centers the sensors 186, 188 in the middle of the vessel V. The deformable legs 210, 212, 214 are thinly sized to limit their impact on the blood flow in the vessel. In this way, the sensors 186, 188 are positioned in the ideal location within the vessel to obtain the best possible reading of the fluid, including such characteristics as pressure and flow.

At 308, the sensors 186, 188 and/or the IVUS array 189 measure pressure and/or flow within the vessel. Signals representing the pressure and/or flow are communicated from the sensors or IVUS array to the processing and communication system 130. The pressure or flow information may be stored or utilized in real time to determine the pressure or flow of fluid within the vessel. In some embodiments, this information is transmitted via the transmitter 140 to the user interface 110 for communication to the clinician.

At 310, the vessel size is estimated. This may be accomplished using any of a variety of methods. In some embodiments, the vessel size is determined using the catheter 160. In other embodiments, the vessel size is determined using methods not involving the catheter 160. One method of determining the vessel size includes utilizing the centering assembly 204 in FIG. 1. In this example the catheter 160, along with the processing and communication system 130, detect the amount of expansion of the centering assembly 204 until the centering assembly 204 comes into contact with the vessel walls. When the centering assembly 204 is in contact with the vessel walls, the diameter of the centering assembly 204 indicates or corresponds to the diameter of the vessel. The diameter of the centering assembly 204 may be determined by tracking the amount of displacement of the pull wires 140 and 142, using sensors or measurement devices that detect that amount of displacement of the distal portion 194, or otherwise taking readings or measurements of the catheter 160. In yet other embodiments, the expanded centering assembly 204 may be measured using fluoroscopic images. The centering assembly 204 may then be used as a reference to estimate the patient vessel size, which may be input or entered at the user interface 110. Other embodiments do not require measuring the vessel relative to the centering assembly 204, but include measuring the vessel using other means or reference points. Embodiments including IVUS imaging array 189 may be used to estimate the vessel size through imaging or other means. If not detected and automatically input to the processing and communication system 130, the clinician may manually input the vessel size using the user interface 110.

In some instances, the procedure includes advancing to a target location proximal of a stenotic lesion and taking measurements, then advancing to a second target location distal of the stenotic lesion and taking additional measurements. These results of the two measurements at locations proximal and distal of the stenotic lesion may then be processed in the manner discussed herein.

At 312, the processing and communication system 130 calculates an offset correlation based on both the vessel size and the catheter size. The offset correlation may be a function of the ratio between vessel size and the catheter size. The processing and communication system 130 may be configured to determine the correlation function and may automatically determine the offset correlation when both the vessel size and the catheter size are determined. In some embodiments, this includes taking into account the vessel size, the catheter size, and the measured data obtained via the sensors 186 and 188.

At 314, the processing and communication system 130 assesses the severity of a stenosis in a blood vessel by calculating FFR for the vessel taking into account the offset correlation. Since the FFR is calculated taking into account the offset correlation, including both the vessel size and catheter size, the FFR may be more accurate than other efforts at determining FFR that rely solely on the size of the catheter while failing to take into account the vessel size. The calculated FFR for the vessel may then be transmitted to the user interface and displayed to the user.

The calculated FFR may take into account the offset correlation and the change in pressure across a stenosis in a vessel. This may be represented by the equation:

$$FFR = \Delta P \cdot \beta$$

where $\Delta P$ is the change in pressure across a stenosis and $\beta$ is the offset correlation. According to one exemplary embodiment, $\Delta P$ is determined by the equation set out below:

$$\Delta P = \frac{8\pi\mu L}{A_s}\frac{1}{A_s}Q + \frac{\rho k}{2}\left(\frac{1}{A_s} - \frac{1}{A_n}\right)^2 Q^2$$

where $\Delta P$ is the pressure loss across the stenosis, $\mu$ is absolute blood viscosity, L is stenosis length, $A_n$ is the cross-sectional area of the normal artery, $A_s$ is the cross sectional area of the stenotic segment, $\rho$ is blood density, k is a constant related to entrance and exit effects, and Q is volume flow. In addition to the catheter cross-sectional area, a further factor may be added to account for the increase in cross-sectional obstructions and flow disturbance caused by the centering assembly.

In some embodiments, the FFR is first calculated based upon measurements accomplished with taking the catheter size and pressure into account. The offset correlation may then be used to calculate a corrected FFR that is more accurate than the FFR.

While described with the processing and communication system 130 determining the correlation factor and calculating the FFR, it should be understood that some embodiments include processing capability on the user interface 110. The user interface or other processing system may be used to determine the correlation factor, the sizes of the catheter or the vessel, or other information utilized to calculate the FFR.

With reference to the above described embodiments, the guidewire lumen includes an internal diameter that is sized and shaped to accommodate the passage of a standard guidewire. The internal diameter may range from 0.014 in. to 0.40 in. In one embodiment, the internal diameter is 0.016 in. to slidingly accommodate a 0.014 in. diameter guidewire. In one embodiment, the internal diameter is 0.024 in. In one embodiment, the internal diameter is 0.018 in. In another embodiment, the internal diameter is 0.038 in. to accommodate a 0.035 in. diameter guidewire. The catheter includes an outer diameter that is sized and shaped to traverse bodily passageways. In the pictured embodiment, the outer diameter is sized to allow passage of the catheter through vascular passageways. In some instances, as mentioned above, the body has an external diameter ranging from 0.014 inches to 0.050 inches. In one embodiment, the outer diameter is 0.024 in. with an internal diameter of about 0.016 in. In one embodiment, the outer diameter is 0.018 in. In another embodiment, the outer diameter is 0.035 in.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. For example, the pressure-sensing catheters disclosed herein may be utilized anywhere with a patient's body, including both arterial and venous vessels, having an indication for pressure measurement. It is understood that such variations may be made to the foregoing without departing from the scope of the present disclosure. Accordingly, it is appropriate that the appended claims be construed broadly and in a manner consistent with the present disclosure.

We claim:

1. An apparatus for assessing the severity of stenosis in a blood vessel, comprising:
    a processor configured for communication with an intravascular catheter positionable within the blood vessel, wherein the processor is configured to:
        receive physiological data of the blood vessel from a first sensor of the intravascular catheter;
        receive, from at least one of a second sensor of the intravascular catheter or an x-ray imaging device, data representing a degree of expansion of a centering assembly of the intravascular catheter;
        receive data representing a size of the intravascular catheter;
        calculate an offset correlation based on:
            the data representing the size of the intravascular catheter; and
            the data representing the degree of expansion of the centering assembly;
        calculate a flow reserve index representative of an impact to blood flow based on the physiological data and the offset correlation; and
        output the flow reserve index to a display in communication with the processor.

2. The apparatus of claim 1, further comprising:
    the intravascular catheter, wherein the intravascular catheter further comprises an elongate body including a proximal portion and a distal portion, the elongate body defining a lumen extending through at least the distal portion, the lumen sized and shaped to allow passage of a guidewire therethrough,
    wherein the centering assembly is disposed at the distal portion of the elongate body, the centering assembly being actuatable to selectively center the elongate body in the blood vessel, and wherein the first sensor is disposed adjacent the centering assembly.

3. The apparatus of claim 1, wherein the flow reserve index comprises a ratio of the physiological data.

4. The apparatus of claim 1, wherein the processor is configured to receive the data representing the degree of expansion of the centering assembly based on measurements taken by the second sensor of the centering assembly.

5. The apparatus of claim 1, wherein the processor is configured to determine a size of the blood vessel based on the degree of expansion of the centering assembly, and wherein the offset correlation is based on a ratio of the size of the intravascular catheter to the size of the blood vessel.

6. The apparatus of claim 5, wherein the size of the intravascular catheter and the size of the vessel are diametrical measurements.

7. The apparatus of claim 5, wherein the size of the intravascular catheter and the size of the vessel are cross-sectional area measurements.

8. The apparatus of claim 1, wherein the centering assembly comprises an expandable portion comprising a proximal expandable portion fixed in place relative to the intravascular catheter and a distal expandable portion moveable on the intravascular catheter.

9. The apparatus of claim 8, wherein the expandable portion comprises legs extending between the proximal expandable portion and the distal expandable portion, the legs being flexible to expand radially outwardly when the distal expandable portion is moved relative to the proximal expandable portion.

10. The apparatus of claim 1, wherein, to receive the data representing the size of the intravascular catheter, the processor is configured to receive an input from a user interface indicating the size of the intravascular catheter.

11. The apparatus of claim 1, wherein, to receive the data representing the size of the intravascular catheter, the processor is configured to access the data representing the size of the intravascular catheter from a memory in communication with the processor.

12. The apparatus of claim 1, wherein, to receive the data representing the size of the intravascular catheter, the processor is configured to automatically receive the data representing the size of the intravascular catheter when the intravascular catheter is connected to the processor.

13. The apparatus of claim 1, wherein the second sensor comprises an intravascular ultrasound (IVUS) sensor, and wherein the data representing the size of the blood vessel comprises IVUS image data obtained by the IVUS sensor.

14. The apparatus of claim 1, wherein the first sensor comprises at least one of a pressure sensor, a flow sensor, or an imaging sensor.

* * * * *